United States Patent [19]

Bundy

[11] 4,174,456
[45] Nov. 13, 1979

[54] 9-DEOXY-9-METHYLENE-INTER-OXA-13,14-DIDEHYDRO-16-PHENYL-17,18,19,20-TETRANOR-PGF$_1$ COMPOUNDS

[75] Inventor: Gordon L. Bundy, Portage, Mich.

[73] Assignee: The Upjohn Company, Kalamazoo, Mich.

[21] Appl. No.: 924,031

[22] Filed: Jul. 12, 1978

Related U.S. Application Data

[63] Continuation-in-part of Ser. No. 786,249, Apr. 11, 1977, Pat. No. 4,118,584.

[51] Int. Cl.$^2$ ............................................. C07C 177/00
[52] U.S. Cl. ......................................... 560/60; 560/55; 260/343.41; 562/470; 562/465
[58] Field of Search .................... 560/60, 55; 562/470; 260/343

[56] References Cited

PUBLICATIONS

Derwent Abstract 79369y/45 Be 854-271, 4-11-77.

*Primary Examiner*—Paul J. Killos
*Attorney, Agent, or Firm*—Robert A. Armitage

[57] ABSTRACT

The present invention relates to novel 9-deoxy-9-methylene-interoxa-13,14-didehydro-16-phenyl-17,18,19,20-tetranor-PGF$_1$ compounds. These compounds are useful pharmacological agents, and are useful for the same purposes as the corresponding PGE-type compounds.

41 Claims, No Drawings

9-DEOXY-9-METHYLENE-INTER-OXA-13,14-DIDEHYDRO-16-PHENYL-17,18,19,20-TETRANOR-PGF$_1$ COMPOUNDS

CROSS REFERENCE TO RELATED APPLICATIONS

The present application is a continuation-in-part of Ser. No. 786,249, filed Apr. 11, 1977, now issued as U.S. Pat. No. 4,118,584.

The present invention relates to novel 9-deoxy-9-methyleneinter-oxa-13,14-didehydro-16-phenyl-17,18,19,20-tetranor-PGF$_1$ compounds, the essential material constituting a disclosure of which is incorporated here by reference from U.S. Pat. No. 4,118,584.

I claim:

1. A prostaglandin analog of the formula

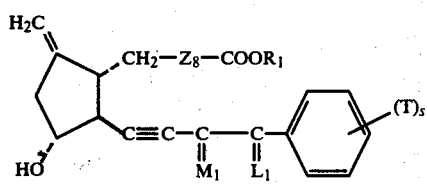

wherein
M$_1$ is

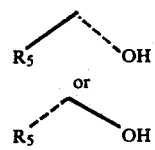

or

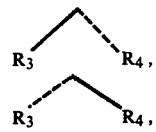

wherein
R$_5$ is hydrogen or methyl;
wherein
L$_1$ is

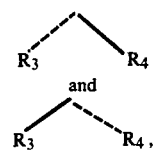

or a mixture of wherein
R$_3$ and R$_4$ are hydrogen, methyl, or fluoro, being the same or different, with the proviso that one of R$_3$ and R$_4$ is fluoro only when the other is hydrogen or fluoro;
wherein Z$_8$ is —CH$_2$—O—CH$_2$—(CH$_2$)$_g$—CH$_2$—
wherein g is one, 2, or 3; wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;

wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alky of one to 3 carbon atoms, inclusive, or a pharmacologically acceptable cation, and the 1,11- or 1,15-lactones thereof.

2. A prostaglandin analog according to claim 1, wherein M$_1$ is

3. A prostaglandin analog according to claim 2, wherein g is 3.

4. 9-Deoxy-9-methylene-2a,2b-dihomo-15-methyl-16-phenyl-17,18,19,20-tetranor-13,14-didehydro-5-oxa-PGF$_1$, a prostaglandin analog according to claim 3.

5. 9-Deoxy-9-methylene-2a,2b-dihomo-15-epi-16-phenyl-17,18,19,20-tetranor-13,14-didehydro-5-oxa-PGF$_1$, a prostaglandin analog according to claim 3.

6. A prostaglandin analog according to claim 2, wherein g is 1.

7. A prostaglandin analog according to claim 6, wherein at least one of R$_3$ and R$_4$ is methyl.

8. 9-Deoxy-9-methylene-15-epi-16-methyl-16-phenyl-18,19,20-trinor-13,14-didehydro-5-oxa-PGF$_1$, a prostaglandin analog according to claim 7.

9. A prostaglandin analog according to claim 6, wherein at least one of R$_3$ and R$_4$ is fluoro.

10. 9-Deoxy-9-methylene-15-epi-16,16-difluoro-16-phenyl-17,18,19-20-tetranor-13,14-didehydro-5-oxa-PGF$_1$, a prostaglandin analog according to claim 9.

11. A prostaglandin analog according to claim 6, wherein R$_3$ and R$_4$ are both hydrogen.

12. 9-Deoxy-9-methylene-15-epi-16-methyl-16-phenyl-17,18,19,20-tetranor-13,14-didehydro-5-oxa-PGF$_1$, a prostaglandin analog according to claim 11.

13. A prostaglandin analog to claim 1, wherein M$_1$ is

14. A prostaglandin analog according to claim 13, wherein s is zero or one and T is chloro, fluoro, or trifluoromethyl.

15. A prostaglandin analog according to claim 14, wherein g is 3.

16. A prostaglandin analog according to claim 15, wherein at least one of R$_3$ and R$_4$ is methyl.

17. 9-Deoxy-9-methylene-2a,2b-dihomo-16-methyl-16-phenyl-18,19,-20-trinor-13,14-didehydro-5-oxa-PGF$_1$, a prostaglandin analog according to claim 16.

18. A prostaglandin analog according to claim 15, wherein at least one of R$_3$ and R$_4$ is fluoro.

19. 9-Deoxy-9-methylene-2a,2b-dihomo-16,16-difluoro-16-phenyl-17,18,19,20-tetranor-13,14-didehydro-5-oxa-PGF$_1$, a prostaglandin analog according to claim 18.

20. A prostaglandin analog according to claim 15, wherein R$_3$ and R$_4$ are both hydrogen.

21. 9-Deoxy-9-methylene-2a,2b-dihomo-16-phenyl-17,18,19,20-tetranor-13,14-didehydro-5-oxa-PGF$_1$, a prostaglandin analog according to claim 20.

22. A prostaglandin analog according to claim 14, wherein g is 1.

23. A prostaglandin analog according to claim 22, wherein at least one of $R_3$ and $R_4$ is methyl.

24. A prostaglandin analog according to claim 23, wherein $R_3$ and $R_4$ are both methyl.

25. 9-Deoxy-9-methylene-16-methyl-16-phenyl-18,19,20-trinor-13,14-didehydro-5-oxa-$PGF_1$, tris-(hydroxymethyl)aminomethane salt, a prostaglandin analog according to claim 24.

26. 9-Deoxy-9-methylene-16-methyl-16-phenyl-18,19,20-trinor-13,14-didehydro-5-oxa-$PGF_1$, methyl ester, a prostaglandin analog according to claim 24.

27. 9-Deoxy-9-methylene-16-methyl-16-phenyl-18,19,20-trinor-13,14-didehydro-5-oxa-$PGF_1$, a prostaglandin analog according to claim 24.

28. A prostaglandin analog according to claim 22, wherein at least one of $R_3$ and $R_4$ is fluoro.

29. A prostaglandin analog according to claim 28, wherein $R_3$ and $R_4$ are both fluoro.

30. A prostaglandin analog according to claim 29, wherein $R_5$ is methyl.

31. 9-Deoxy-9-methylene-15-methyl-16,16-difluoro-16-phenyl-17,18,19,20-tetranor-13,14-didehydro-5-oxa-$PGF_1$, a prostaglandin analog according to claim 28.

32. A prostaglandin analog according to claim 29, wherein $R_5$ is hydrogen.

33. 9-Deoxy-9-methylene-16,16-difluoro-16-phenyl-17,18,19,20-tetranor-13,14-didehydro-5-oxa-$PGF_1$, a prostaglandin analog according to claim 32.

34. A prostaglandin analog according to claim 22, wherein $R_3$ and $R_4$ are both hydrogen.

35. A prostaglandin analog according to claim 34, wherein $R_5$ is methyl.

36. 9-Deoxy-9-methylene-15-methyl-16-phenyl-17,18,19,20-tetranor-13,14-didehydro-5-oxa-$PGF_1$, tris-(hydroxymethyl)aminomethane salt, a prostaglandin analog according to claim 35.

37. 9-Deoxy-9-methylene-15-methyl16-phenyl-17,18,19,20-tetranor-13,14-didehydro-5-oxa-$PGF_1$, methyl ester, a prostaglandin analog according to claim 35.

38. 9-Deoxy-9-methylene-15-methyl-16-phenyl-17,18,19,20-tetranor-13,14-didehydro-5-oxa-$PGF_1$, a prostaglandin analog according to claim 35.

39. A prostaglandin analog according to claim 34, wherein $R_5$ is hydrogen.

40. 9-Deoxy-9-methylene-16-phenyl-17,18,19,20-tetranor-13,14-didehydro-5-oxa-$PGF_1$, methyl ester, a prostaglandin analog according to claim 39.

41. 9-Deoxy-9-methylene-16-phenyl-17,18,19,20-tetranor-13,14-didehydro-5-oxa-$PGF_1$, a prostaglandin analog according to claim 39.

* * * * *

UNITED STATES PATENT OFFICE
CERTIFICATE OF CORRECTION

Patent No. 4,174,456　　　　　　　　Dated 13 November 1979

Inventor(s) Gordon L. Bundy

It is certified that error appears in the above-identified patent and that said Letters Patent are hereby corrected as shown below:

Column 2, line 17, "15-methyl-" should read -- 15-epi-15-methyl- --; line 38, "15-epi-16-methyl-" should read -- 15-epi-15-methyl- --.

Signed and Sealed this

Seventeenth Day of June 1980

[SEAL]

Attest:

SIDNEY A. DIAMOND

*Attesting Officer*　　　*Commissioner of Patents and Trademarks*